(12) United States Patent
Gannon et al.

(10) Patent No.: US 11,737,777 B2
(45) Date of Patent: Aug. 29, 2023

(54) TISSUE RESECTING INSTRUMENTS

(71) Applicant: Covidien LP, Mansfield, MA (US)

(72) Inventors: Alan P. Gannon, Amesbury, MA (US); Nikolai D. Begg, Wellesley, MA (US); Dalia P. Leibowitz, Cambridge, MA (US)

(73) Assignee: Covidien LP, Mansfield, MA (US)

( * ) Notice: Subject to any disclaimer, the term of this patent is extended or adjusted under 35 U.S.C. 154(b) by 107 days.

(21) Appl. No.: 17/167,481

(22) Filed: Feb. 4, 2021

(65) Prior Publication Data

US 2021/0236155 A1 Aug. 5, 2021

Related U.S. Application Data

(60) Provisional application No. 62/970,519, filed on Feb. 5, 2020.

(51) Int. Cl.
*A61B 17/3205* (2006.01)
*A61B 17/42* (2006.01)

(52) U.S. Cl.
CPC .......... *A61B 17/3205* (2013.01); *A61B 17/42* (2013.01); *A61B 2017/4216* (2013.01); *A61B 2217/005* (2013.01); *A61B 2217/007* (2013.01)

(58) Field of Classification Search
CPC ........ A61B 17/3205; A61B 17/320758; A61B 17/32002; A61B 17/320783; A61B 2017/320032; A61B 2017/320791; A61B 2217/005; A61B 2217/007; A61B 17/1715; A61B 17/34; A61B 17/3421; A61F 9/00763; B23B 51/02

See application file for complete search history.

(56) References Cited

U.S. PATENT DOCUMENTS

| | | | |
|---|---|---|---|
| 1,585,934 A | 5/1926 | Muir | |
| 1,666,332 A | 4/1928 | Hirsch | |
| 1,831,786 A | 11/1931 | Duncan | |
| 2,708,437 A | 5/1955 | Hutchins | |
| 3,082,805 A | * 3/1963 | Royce | G01N 1/286 600/568 |
| 3,297,022 A | 1/1967 | Wallace | |
| 3,686,706 A | 8/1972 | Finley | |
| 3,732,858 A | * 5/1973 | Banko | A61B 17/32002 606/107 |
| 3,734,099 A | 5/1973 | Bender et al. | |
| 3,791,379 A | 2/1974 | Storz | |
| 3,812,855 A | 5/1974 | Banko | |
| 3,835,842 A | 9/1974 | Iglesias | |
| 3,850,162 A | 11/1974 | Iglesias | |

(Continued)

FOREIGN PATENT DOCUMENTS

| | | |
|---|---|---|
| DE | 3339322 A1 | 5/1984 |
| DE | 3206381 C2 | 7/1986 |

(Continued)

*Primary Examiner* — Diane D Yabut
*Assistant Examiner* — Christian D Knauss
(74) *Attorney, Agent, or Firm* — Carter, DeLuca & Farrell LLP

(57) ABSTRACT

A tissue resecting instrument includes a housing, a shaft extending distally from the housing and rotatable relative to the housing, and a tissue cutting extending distally from the shaft. The tissue cutter provides for both radial and distal resection of tissue.

20 Claims, 4 Drawing Sheets

(56) References Cited

U.S. PATENT DOCUMENTS

| | | |
|---|---|---|
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Fhimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,775,365 A * | 10/1988 | Swartz .............. A61M 1/842 137/625.22 |
| 4,819,635 A * | 4/1989 | Shapiro ............ A61F 9/00763 600/565 |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,971,034 A | 11/1990 | Doi et al. |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,242,460 A * | 9/1993 | Klein ............ A61B 17/320783 606/159 |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,575,756 A | 11/1996 | Karasawa et al. |
| 5,586,973 A | 12/1996 | Lemaire et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,690,634 A * | 11/1997 | Muller ............... A61B 17/164 606/180 |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |

(56) References Cited

U.S. PATENT DOCUMENTS

| | | |
|---|---|---|
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,025,656 B2 | 9/2011 | Gruber et al. |
| 8,061,359 B2 | 11/2011 | Emanuel |
| 8,062,214 B2 | 11/2011 | Shener et al. |
| 8,419,626 B2 | 4/2013 | Shener-Irmakoglu et al. |
| 8,465,421 B2 | 6/2013 | Finkman et al. |
| 8,528,563 B2 | 9/2013 | Gruber |
| 8,574,253 B2 | 11/2013 | Gruber et al. |
| 8,647,349 B2 | 2/2014 | Gruber et al. |
| 8,663,264 B2 | 3/2014 | Cesarini et al. |
| 8,678,999 B2 | 3/2014 | Isaacson |
| 8,834,487 B2 | 9/2014 | Gruber et al. |
| 8,840,625 B2 | 9/2014 | Adams et al. |
| 8,840,626 B2 | 9/2014 | Adams et al. |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,060,760 B2 | 6/2015 | Sullivan et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,095,366 B2 | 8/2015 | Sullivan et al. |
| 9,125,550 B2 | 9/2015 | Shener-Irmakoglu et al. |
| 9,155,454 B2 | 10/2015 | Sahney et al. |
| 9,259,233 B2 | 2/2016 | Gruber et al. |
| 10,080,571 B2 | 9/2018 | Davis et al. |
| 10,357,259 B2 | 7/2019 | Bowman et al. |
| 2003/0114875 A1* | 6/2003 | Sjostrom .......... A61B 17/32002 606/170 |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber et al. |
| 2008/0097471 A1 | 4/2008 | Adams et al. |
| 2008/0114364 A1 | 5/2008 | Goldin et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0082628 A1 | 3/2009 | Kucklick et al. |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0087798 A1 | 4/2010 | Adams et al. |
| 2010/0152647 A1 | 6/2010 | Shener et al. |
| 2011/0034943 A1 | 2/2011 | Churchill et al. |
| 2011/0077674 A1 | 3/2011 | Sullivan et al. |
| 2011/0118544 A1 | 5/2011 | Adams et al. |
| 2011/0166419 A1 | 7/2011 | Reif et al. |
| 2012/0067352 A1 | 3/2012 | Gruber et al. |
| 2012/0078038 A1 | 3/2012 | Sahney et al. |
| 2012/0130274 A1* | 5/2012 | Persat ................ A61B 10/0275 600/564 |
| 2013/0110145 A1* | 5/2013 | Weitzman ........ A61B 17/00234 606/170 |
| 2013/0131452 A1 | 5/2013 | Kuroda et al. |
| 2013/0324996 A1* | 12/2013 | Pellegrino .......... A61B 17/8819 606/33 |
| 2014/0003183 A1 | 1/2014 | Song |

FOREIGN PATENT DOCUMENTS

| | | |
|---|---|---|
| DE | 3601453 A1 | 9/1986 |
| DE | 3615694 A1 | 11/1987 |
| DE | 4038398 A1 | 6/1992 |
| DE | 4440035 A1 | 5/1996 |
| DE | 19633124 A1 | 5/1997 |
| DE | 19751632 C1 | 9/1999 |
| DE | 102006022827 A1 | 12/2006 |
| EP | 0310285 A2 | 4/1989 |
| EP | 0327410 A1 | 8/1989 |
| EP | 0557044 A1 | 8/1993 |
| EP | 0582295 A2 | 2/1994 |
| EP | 0606531 A2 | 7/1994 |
| EP | 0621008 A2 | 10/1994 |
| EP | 0806183 A1 | 11/1997 |
| EP | 1681022 A1 | 7/2006 |
| GB | 2093353 A | 9/1982 |
| GB | 2311468 A | 10/1997 |
| JP | 2001075416 A | 3/2001 |
| JP | 2002529185 A | 9/2002 |
| JP | 2002538889 A | 11/2002 |
| JP | 2003245247 A | 9/2003 |
| NL | 1006944 C2 | 3/1999 |
| WO | 8101648 A1 | 6/1981 |
| WO | 9211816 A2 | 7/1992 |
| WO | 9307821 A1 | 4/1993 |

(56) References Cited

FOREIGN PATENT DOCUMENTS

| | | |
|---|---|---|
| WO | 9315664 A1 | 8/1993 |
| WO | 9426181 A1 | 11/1994 |
| WO | 9505777 A1 | 3/1995 |
| WO | 9510981 A1 | 4/1995 |
| WO | 9510982 A1 | 4/1995 |
| WO | 9522935 A1 | 8/1995 |
| WO | 9530377 A1 | 11/1995 |
| WO | 9611638 A1 | 4/1996 |
| WO | 9626676 A1 | 9/1996 |
| WO | 9709922 A1 | 3/1997 |
| WO | 9717027 A1 | 5/1997 |
| WO | 9719642 A1 | 6/1997 |
| WO | 9724071 A1 | 7/1997 |
| WO | 9734534 A1 | 9/1997 |
| WO | 9735522 A1 | 10/1997 |
| WO | 9809569 A1 | 3/1998 |
| WO | 9810707 A1 | 3/1998 |
| WO | 9846147 A1 | 10/1998 |
| WO | 9903407 A1 | 1/1999 |
| WO | 9903409 A1 | 1/1999 |
| WO | 9907295 A1 | 2/1999 |
| WO | 9911184 A1 | 3/1999 |
| WO | 9939648 A1 | 8/1999 |
| WO | 9944506 A1 | 9/1999 |
| WO | 9960935 A1 | 12/1999 |
| WO | 0012010 A1 | 3/2000 |
| WO | 0028890 A1 | 5/2000 |
| WO | 0033743 A1 | 6/2000 |
| WO | 0044295 A1 | 8/2000 |
| WO | 0047116 A1 | 8/2000 |
| WO | 0057797 A1 | 10/2000 |
| WO | 0135831 A1 | 5/2001 |
| WO | 0158368 A1 | 8/2001 |
| WO | 0195810 A2 | 12/2001 |
| WO | 02069808 A2 | 9/2002 |
| WO | 03022164 A1 | 3/2003 |
| WO | 03077767 A1 | 9/2003 |
| WO | 2005060842 A1 | 7/2005 |
| WO | 2005096963 A2 | 10/2005 |
| WO | 2006105283 A2 | 10/2006 |
| WO | 2006121968 A2 | 11/2006 |
| WO | 2006121970 A2 | 11/2006 |
| WO | 2007044833 A2 | 4/2007 |
| WO | 2012044705 A1 | 4/2012 |

* cited by examiner

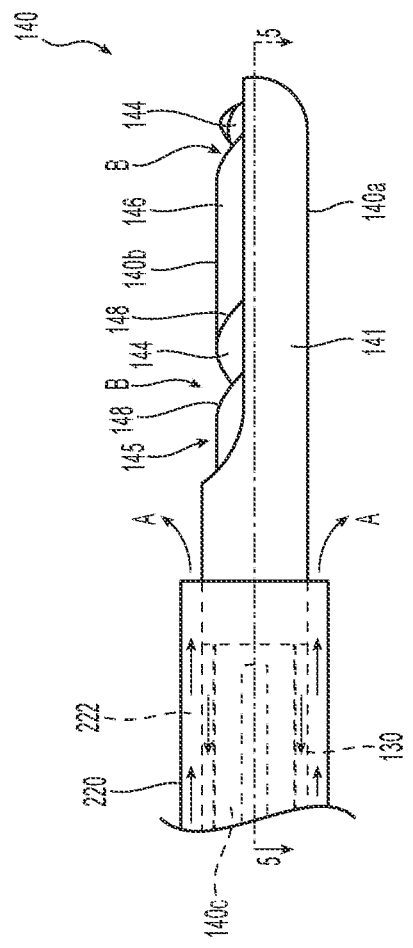
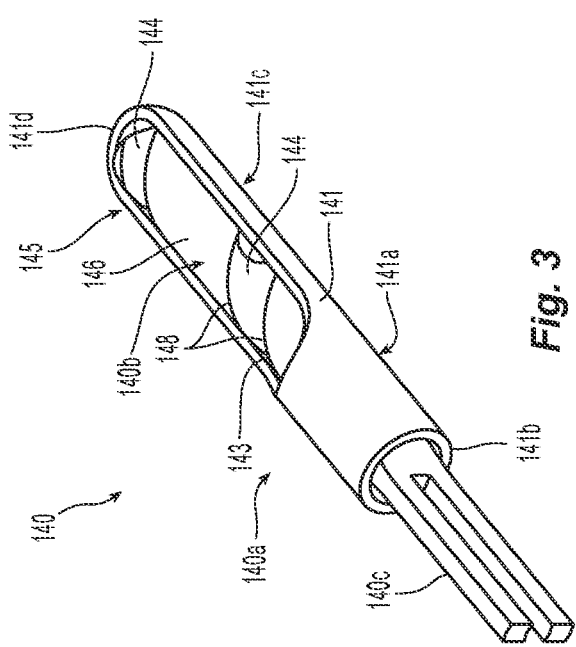

TISSUE RESECTING INSTRUMENTS

CROSS-REFERENCE TO RELATED APPLICATIONS

This application claims the benefit of and priority to U.S. Provisional Patent Appl. No. 62/970,519, filed Feb. 5, 2020, the entire content of which is incorporated herein by reference.

FIELD

The present technology relates generally to the field of tissue resection. In particular, the present technology relates to a tissue cutter of a tissue resecting instrument.

BACKGROUND

Tissue resection may be performed endoscopically within an organ, such as a uterus, by inserting an endoscope into the uterus and passing a tissue resecting instrument through the endoscope and into the uterus. Tissue resecting instruments include electrosurgical instruments using, for example, high-frequency electrical current, and/or mechanical surgical instruments using, for example, a cutting blade, to remove tissue.

SUMMARY

Techniques of this disclosure generally relate to a tissue resecting instrument including a tissue cutter for effectively resecting soft and dense tissue, and evacuating the resected tissue through the tissue resecting instrument.

In one aspect, the disclosure provides a tissue resecting instrument including a housing, a shaft, and a tissue cutter. The shaft extends distally from the housing and is rotatable relative to the housing, and the tissue cutter extends distally from the shaft. The tissue cutter includes and outer shroud and an inner cutting member. The outer shroud includes a cylindrical body having a proximal portion and distal portion terminating at a distal end. The cylindrical body defines a window therein that extends through the distal portion and the distal end. The window has a half cylinder shape such that the distal portion is a half cylinder with half of the distal portion, including half of the distal end, being open. The inner cutting member is disposed within the outer shroud.

The inner cutting member may be fixedly engaged to the shaft such that rotation of the shaft rotates the inner cutting member relative to the outer shroud.

The inner cutting member may include a shank portion disposed within the proximal portion of the outer shroud and a cutting portion disposed within the distal portion of the outer shroud. The cutting portion may include a channel defined in an outer surface thereof that is in open communication with a cavity defined in the outer shroud to define a space between the inner cutting member and the outer shroud. The space defined between the inner cutting member and the outer shroud may be in open communication with a lumen of the shaft. The shank portion may have a diameter that is smaller than a diameter of the cutting portion. The channel may be helical and wind continuously around an entire length of the cutting portion of the inner cutting member.

The tissue resecting instrument may include a fluid outflow tube in open communication with the lumen of the shaft.

The housing may include a drive mechanism disposed therein, the drive mechanism operably coupled to the shaft to drive rotation of the shaft relative to the housing.

In another aspect, the disclosure provides a tissue resecting instrument including a housing, a shaft, and a tissue cutter. The shaft extends distally from the housing and is rotatable relative to the housing. The shaft defines a lumen therethrough. The tissue cutter extends distally from the shaft and is rotatable with the shaft. The tissue cutter defines an opening through an outer surface thereof that is in open communication with the lumen of the shaft. The tissue cutter includes cutting edges disposed within the opening such that the outer surface is free of cutting edges.

The opening and/or the cutting edges may be helically wound around a cylindrical body of the tissue cutter.

The tissue resecting instrument may include a fluid outflow tube in open communication with the lumen of the shaft. The tissue resecting instrument may include a suction source operably coupled to the fluid outflow tube.

The housing may include a drive mechanism disposed therein, the drive mechanism operably coupled to the shaft to drive rotation of the shaft relative to the housing.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIG. 3 is a perspective view of a tissue cutter of the tissue resecting instrument of FIG. 2;

FIG. 4 is a side view of a distal end portion of the tissue resecting system of FIG. 1;

DETAILED DESCRIPTION

Figure 1:
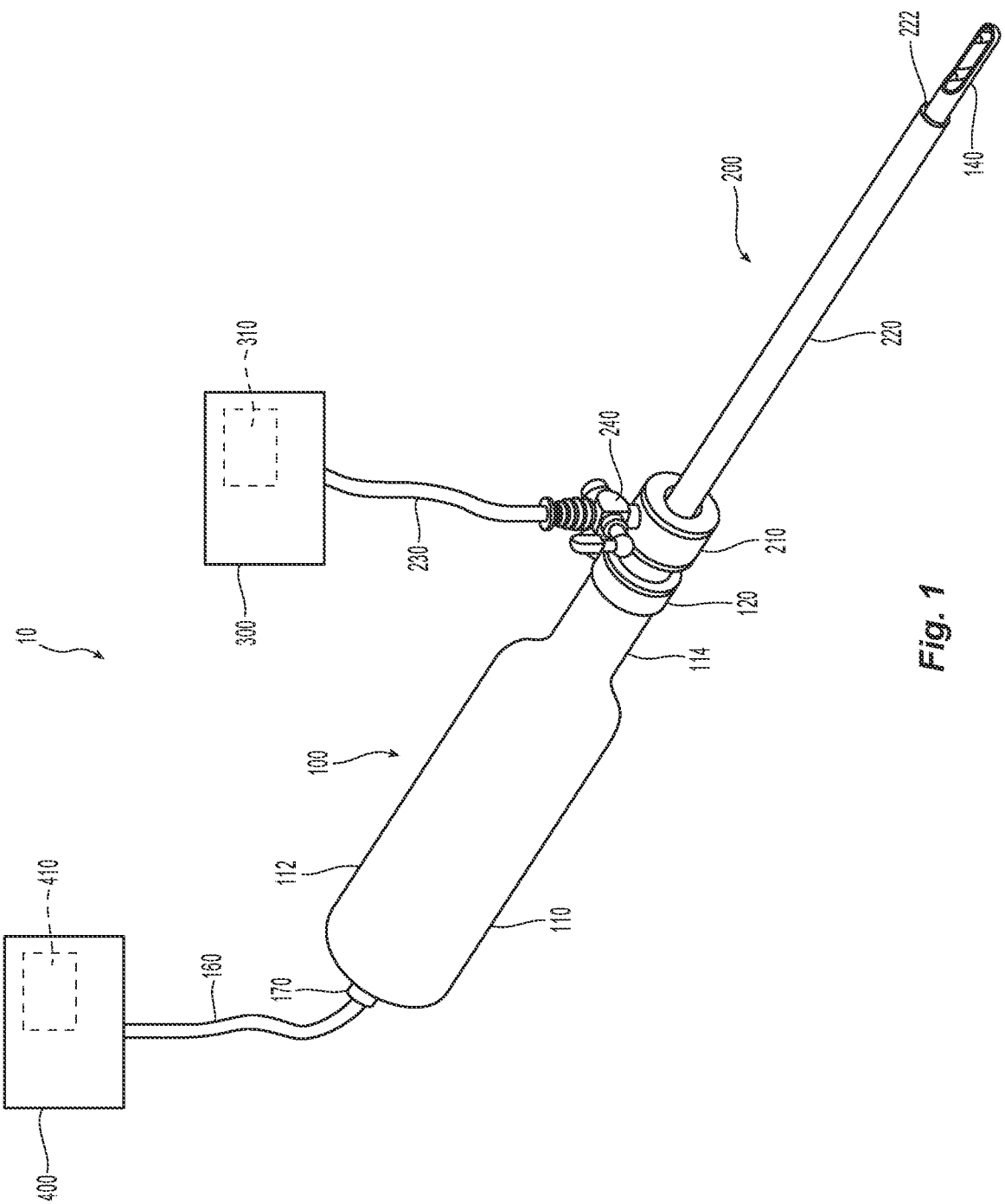
FIG. 1 is a perspective view of a tissue resecting system in accordance with an aspect of the disclosure.

Embodiments of the disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Like reference numerals may refer to similar or identical elements throughout the description of the figures. As shown in the drawings and described throughout the following description, as is traditional when referring to relative positioning of a surgical instrument, the term "proximal" refers to a portion (e.g., an end) of the apparatus which is closer to the user and the term "distal" refers to a portion of the apparatus which is farther away from the user.

Figure 2:
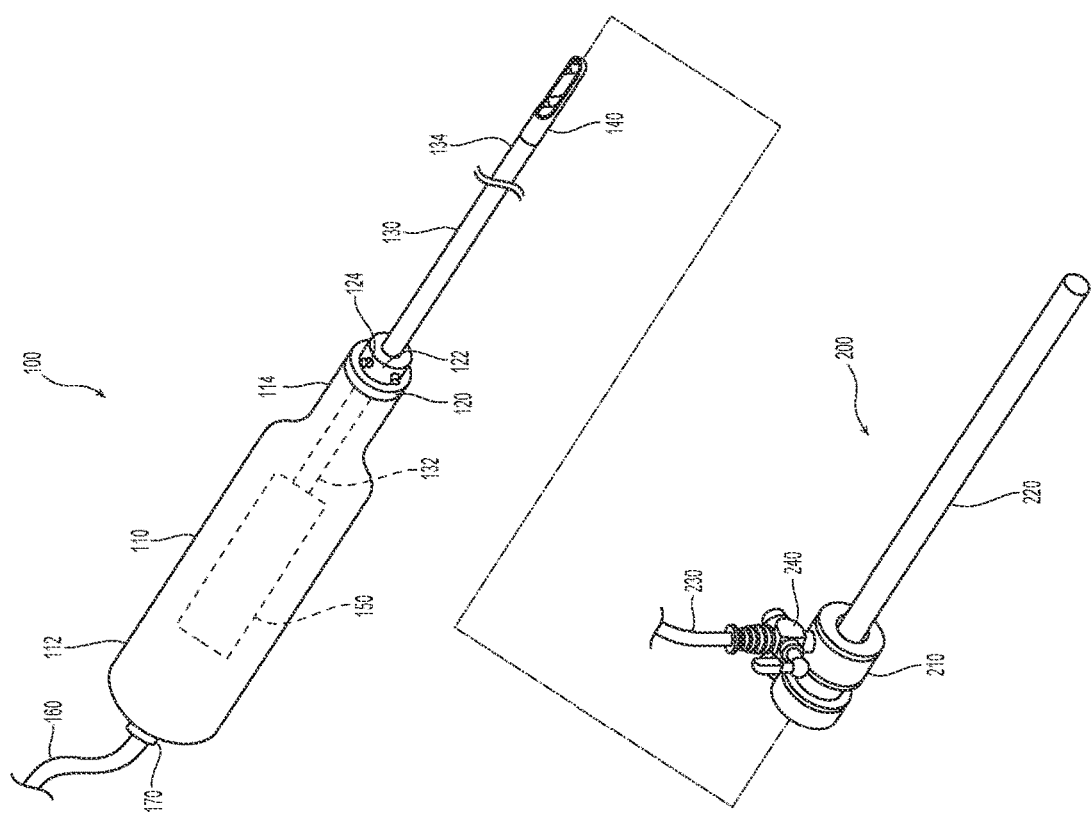
FIG. 2 is an exploded, perspective view of a tissue resecting instrument and an outer sheath of the tissue resecting system of FIG. 1.

Referring to FIGS. 1 and 2, a tissue resecting system 10 in accordance with the disclosure includes a tissue resecting instrument 100, an outer assembly 200 configured to removably couple to the tissue resecting instrument 100 (although, in embodiments, the outer assembly 200 may be integral with the tissue resecting instrument 100), a fluid pump 300 including a fluid supply reservoir 310 associated therewith, and a suction source 400 including a fluid collecting reservoir 410 associated therewith. The tissue resecting system 10 may be used in conjunction with a suitable endoscope (not shown) or may be used independently thereof. As detailed below, the tissue resecting system 10 is configured to facilitate the resection of tissue from within an internal body cavity or organ, e.g., a uterus, while enabling fluid inflow and fluid outflow to maintain proper distension of the uterus during the tissue resection procedure, flush tissue and other debris from within the uterus, and maintain a visible working space.

The tissue resecting instrument 100 generally includes a housing 110, an outer sheath connector 120, a shaft 130, a tissue cutter or shaver 140, a drive mechanism 150, and a fluid outflow tube 160. The housing 110 defines a body portion 112 and a distal nose portion 114. The outer sheath connector 120 is disposed on the distal nose portion 114 of the housing 110 and includes a collar 122 having a plurality of engagement features, e.g., radially-spaced male bayonet connectors 124, extending radially outwardly from the collar 122. The outer sheath connector 120 is configured to facilitate releasable engagement of the outer assembly 200 with the tissue resecting instrument 10. The fluid outflow tube 160 communicates with the interior of the housing 110 and/or the interior of the shaft 130 to enable the withdrawal, e.g., via suction, of fluid, tissue, and other debris from within the housing 110 and/or the shaft 130. The fluid outflow tube 160 is operably coupled to the suction source 400 to enable suction therethrough and for depositing the suctioned fluid, tissue, and other debris into the fluid collecting reservoir 410. The fluid outflow tube 160 may further include a valve 170 associated therewith for regulating the outflow of fluid from the housing 110 and/or the shaft 130.

The shaft 130 of tissue resecting instrument 100 defines a lumen (not explicitly shown) therethrough, and includes a proximal end portion 132 and a distal end portion 134. The shaft 130 is rotatably coupled to the housing 110 to enable rotation of the shaft 130 relative to the housing 110 about a longitudinal axis of the shaft 130. The proximal end portion 132 of the shaft 130 is disposed within the housing 110. The shaft 130 extends distally from the housing 110 through the outer sheath connector 120 to the distal end portion 134 of the shaft 130. The tissue cutter 140, described in greater detail below, is fixed relative to and extends distally from the distal end portion 134 of the shaft 130. The drive mechanism 150 is operably supported within the body portion 112 of the housing 110 and operably coupled to the proximal end portion 132 of the shaft 130. The drive mechanism 150 is configured to drive rotation of the shaft 130 relative to the housing 110, thus rotating the tissue cutter 140 relative to the housing 110 to resect tissue.

Continuing with FIGS. 1 and 2, the outer assembly 200 includes a proximal hub 210, an outer sheath 220, a fluid inflow tube 230, and a valve 240. The proximal hub 210 is configured for positioning about the collar 122 of the outer sheath connector 120 of the tissue resecting instrument 100 and includes suitable engagement features, e.g., female bayonet connectors (not shown), to enable releasable engagement of the proximal hub 210 about the outer sheath connector 120 and, thus, releasable engagement of the outer assembly 200 about the tissue resecting instrument 100. The outer sheath 220 is fixed relative to and extends distally from the proximal hub 210. Upon engagement of the outer assembly 200 about the tissue resecting instrument 100, the outer sheath 220 of the outer assembly 200 is disposed about the shaft 130 of the tissue resecting instrument 100 so as to define an annular channel 222 between the shaft 130 and the outer sheath 220. The fluid inflow tube 230 of the outer assembly 200 is operably and, in some embodiments, releasably, coupled to the proximal hub 210 with the valve 240 disposed therebetween to enable fluid to be pumped from the fluid supply reservoir 310 into the proximal hub 210 and through the annular channel 222 by way of the fluid pump 300.

Figure 5:
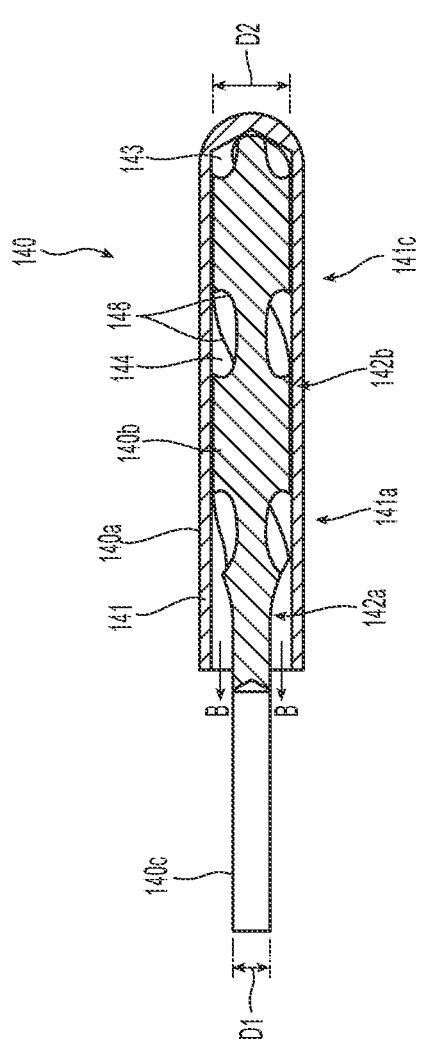
FIG. 5 is a cross-sectional view of a tissue cutter of the tissue resecting system of FIG. 1, taken along section line 5-5 of FIG. 4.

With additional reference to FIGS. 3-5, the tissue cutter 140 of the tissue resection instrument 100 includes an outer shroud or sleeve 140a, an inner cutting member 140b disposed within the outer shroud 140a, and a drive connector 140c extending proximally from the inner cutting member 140. The outer shroud 140a includes a cylindrical body 141 have a proximal portion 141a terminating at a proximal end 141b and a distal portion 141c terminating at a distal end 141d. The cylindrical body 141 defines a cavity 143 therethrough in which the inner cutting member 140b is positioned. The proximal portion 141a of the cylindrical body 141 of the outer shroud 140a is a full cylinder (e.g., has a continuous cylindrical wall) that is open at the proximal end 141b, and the distal portion 141c of the cylindrical body 141 is a half cylinder defining a window 145 therein that extends to the distal end 141d. The window 145 has a half cylinder shape such that half of the distal portion 141c, including half of the distal end 141d, is open, and the inner cutting member 140b is exposed through the window 145.

The inner cutting member 140b includes a shank portion 142a and a cutting portion 142b. The shank portion 142a is disposed within the proximal portion 141a of the outer shroud 140a, and the cutting portion 142b is disposed within the distal portion 141c of the outer shroud 140a. The cutting portion 142b includes a channel or groove 144 defined in an outer surface 146 thereof that is helical in shape and winds continuous around the length of the cutting portion 142b (e.g., from the shank portion 142a to a tip of the cutting portion 142b). The channel 144 is in open communication with the cavity 143 of the outer shroud 140a, and the shank portion 142a has a diameter "D1" that is smaller than a diameter "D2" of the cutting portion 142b creating a space between the outer shroud 140a and the inner cutting member 140b, thereby providing a flow path into the window 145 of the outer shroud 140a, between the outer shroud 140a and the inner cutting member 140b, and into the lumen of the shaft 130. Alternatively, the flow path may be created by hollowing out the inner cutting member 140b to allow fluid to flow therethrough. Cutting edges 148 surround the channel 144 and extend continuously around the length of the cutting portion 142b.

The drive connector 140c extends proximally from the shank portion 142a of the inner cutting member 140b and extends proximally beyond the proximal end 141b of the outer shroud 140a.

The proximal end 141b of the outer shroud 140a abuts the shaft 130 in a fluid tight manner such that the drive connector 140c extends into the shaft 130. The drive connector 140c is connected to the drive mechanism 150 (FIG. 2) and couples the inner cutting member 140b to the shaft 130 such that the inner cutting member 140b is rotatable with the shaft 130 relative to the outer shroud 140a.

In use, inflow fluid is pumped into the surgical site through the annular channel 222 defined between the shaft 130 and the outer sheath 220, as indicated by arrows "A," and outflow fluid is suctioned, along with tissue and other debris, through the window 145 of the outer shroud 140a, into the channel 144 of the inner cutting member 140b, past the shank portion 142a, and through the shaft 130, as indicated by arrows "B." The suctioning of tissue into the channel 144, in combination with the rotation imparted to the tissue cutter 140 by drive mechanism 150 (FIG. 2), enables the resection of tissue using the cutting edges 148 and the suctioning of the resected tissue proximally through shaft 130. The configuration of the window 145 of the outer shroud 140a and the cutting edges 148 of the inner cutting member 140b provides for both radial and distal resection of tissue.

Figure 6:
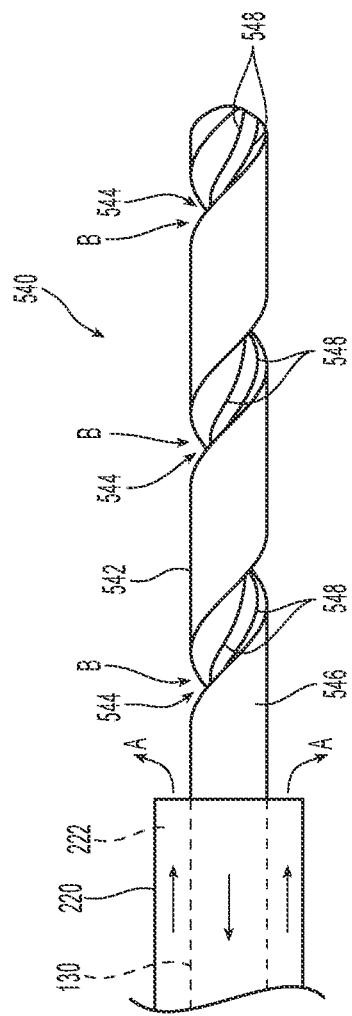
FIG. 6 is a side view of a distal end portion of the tissue resecting system of FIG. 1, including a tissue cutter in accordance with another aspect of the disclosure.

Referring now to FIG. 6, another configuration of the distal end portion of the tissue resecting system 10 (FIG. 1) is provided wherein the shaft 130 includes a tissue cutter 540 extending distally therefrom. The tissue cutter 540 includes a cylindrical body 542 defining an opening 544 through an outer surface 546 thereof providing access to the lumen of the shaft 130. The cylindrical body 542 further includes cutting edges 548 disposed within the opening 544 such that the outer surface 546 is free of cutting edges. The opening 544 and the cutting edges 548 are helically wound around the tissue cutter 540, but other configurations are envisioned in which the cutting edges 548 are disposed radially inwardly of the outer surface 546 of the cylindrical body 542.

In use, inflow fluid is pumped into the surgical site through annular channel 222, as indicated by arrows "A" and outflow fluid is suctioned, along with tissue and other debris, into the opening 544 of the tissue cutter 540 and through the shaft 130, as indicated by arrows "B." The suctioning of tissue into the opening 544, in combination with the rotation imparted to the tissue cutter 540 by the drive mechanism 150 (FIG. 2), enables the resection of tissue using the cutting edges 548, and the suctioning of the resected tissue proximally through shaft 130.

While several embodiments of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the disclosure, and that such modifications and variation are also included within the scope of the disclosure. Therefore, the above description should not be construed as limiting, but merely as exemplifications of embodiments of the disclosure. Thus the scope of the embodiments should be determined by the appended claims and their legal equivalents, rather than by the examples given.

What is claimed is:

1. A tissue resecting instrument, comprising:
    a housing;
    a shaft extending distally from the housing and being rotatable relative to the housing, the shaft including a lumen defined through the shaft from a proximal end of the shaft to a distal end of the shaft; and
    a tissue cutter extending distally from the distal end of the shaft, the tissue cutter including:
        an outer shroud including a cylindrical body having a proximal portion and distal portion terminating at a distal end, the proximal portion of the cylindrical body abutting the distal end of the shaft, the cylindrical body defining a window that extends through the distal portion and the distal end, the window having a half cylinder shape such that the distal portion is a half cylinder with half of the distal portion, including half of the distal end, being open; and
        an inner cutting member disposed within the outer shroud and fixedly engaged to the shaft such that rotation of the shaft rotates the inner cutting member relative to the outer shroud, the tissue cutter having a space defined between the inner cutting member and the outer shroud that is in open communication with the lumen of the shaft to define a flow path into the window of the outer shroud, between the inner cutting member and the outer shroud, and through the lumen of the shaft.

2. The tissue resecting instrument according to claim 1, wherein the inner cutting member includes a shank portion disposed within the proximal portion of the outer shroud and a cutting portion disposed within the distal portion of the outer shroud.

3. The tissue resecting instrument according to claim 2, wherein the cutting portion includes a channel defined in an outer surface of the cutting portion that is in open communication with a cavity defined in the outer shroud, the channel and the cavity defining the space between the inner cutting member and the outer shroud.

4. The tissue resecting instrument according to claim 3, wherein the shank portion has a diameter that is smaller than a diameter of the cutting portion.

5. The tissue resecting instrument according to claim 3, wherein the channel is helical and winds continuously around an entire length of the cutting portion of the inner cutting member.

6. The tissue resecting instrument according to claim 1, further comprising a fluid outflow tube in open communication with the lumen of the shaft.

7. The tissue resecting instrument according to claim 1, wherein the housing includes a drive mechanism disposed in the housing, the drive mechanism operably coupled to the shaft to drive rotation of the shaft relative to the housing.

8. The tissue resecting instrument according to claim 7, wherein the inner cutting member includes a drive connector extending proximally beyond the outer shroud and into the lumen of the shaft, the drive connector operably coupled to the drive mechanism.

9. The tissue resecting instrument according to claim 1, further comprising an outer sheath connector, the outer sheath connector configured to releasably engage an outer assembly including an outer sheath that extends over the shaft and defines an annular channel between the shaft and the outer sheath.

10. The tissue resecting instrument according to claim 9, wherein the outer sheath connector is disposed on a distal nose portion of the housing and includes at least one engagement feature extending outwardly from the housing.

11. The tissue resecting instrument according to claim 9, wherein the outer assembly includes a fluid inflow tube in communication with the annular channel.

12. The tissue resecting instrument according to claim 1, wherein the inner cutting member includes cutting edges, and the outer shroud is free of cutting edges.

13. A tissue resecting instrument, comprising:
a housing;
a shaft extending distally from the housing and being rotatable relative to the housing, the shaft including a lumen defined through the shaft from a proximal end of the shaft to a distal end of the shaft; and
a tissue cutter extending distally from the distal end of the shaft and being rotatable with the shaft, the tissue cutter including a cylindrical body having an opening defined through an outer surface of the cylindrical body that is in open communication with the lumen of the shaft, the cylindrical body including cutting edges disposed within the opening such that the outer surface is free of cutting edges, the cylindrical body defining a distal end of the tissue resecting instrument.

14. The tissue resecting instrument according to claim 13, wherein the opening is helically wound around the cylindrical body of the tissue cutter.

15. The tissue resecting instrument according to claim 14, wherein the cutting edges are helically wound around the cylindrical body of the tissue cutter.

16. The tissue resecting instrument according to claim 13, further comprising a fluid outflow tube in open communication with the lumen of the shaft.

17. The tissue resecting instrument according to claim 16, further comprising a suction source operably coupled to the fluid outflow tube.

18. The tissue resecting instrument according to claim 13, further including a drive mechanism disposed in the housing, the drive mechanism operably coupled to the shaft to drive rotation of the shaft relative to the housing.

19. The tissue resecting instrument according to claim 13, further comprising an outer sheath connector, the outer sheath connector configured to releasably engage an outer assembly including an outer sheath that extends over the shaft and defines an annular channel between the shaft and the outer sheath.

20. The tissue resecting instrument according to claim 13, wherein the tissue cutter includes a channel defined in an outer surface of the cylindrical body, and the opening and the cutting edges are defined in the channel.

* * * * *